United States Patent
Hoy et al.

(10) Patent No.: US 11,821,381 B2
(45) Date of Patent: Nov. 21, 2023

(54) METHOD OF ASSIGNING AN OCTANE NUMBER TO A FUEL

(71) Applicant: ExxonMobil Technology and Engineering Company, Annandale, NJ (US)

(72) Inventors: Randall N. Hoy, Fort Saskatchewan (CA); Jerry D. Foster, Jr., Conroe, TX (US); Jormarie Bitar, Spring, TX (US)

(73) Assignee: ExxonMobil Technology and Engineering Company, Annandale, NJ (US)

( * ) Notice: Subject to any disclaimer, the term of this patent is extended or adjusted under 35 U.S.C. 154(b) by 46 days.

(21) Appl. No.: 17/148,750

(22) Filed: Jan. 14, 2021

(65) Prior Publication Data
US 2022/0220915 A1    Jul. 14, 2022

Related U.S. Application Data

(60) Provisional application No. 62/970,221, filed on Feb. 5, 2020.

(51) Int. Cl.
| | |
|---|---|
| *F02D 41/14* | (2006.01) |
| *F02D 19/06* | (2006.01) |
| *F02D 35/02* | (2006.01) |

(52) U.S. Cl.
CPC ..... *F02D 41/1498* (2013.01); *F02D 19/0649* (2013.01); *F02D 35/027* (2013.01)

(58) Field of Classification Search
CPC ... F02D 41/1497–1498; F02D 19/0649; F02D 35/027; G01L 23/22–227; G01N 33/2817; G01N 33/2829

USPC ...... 73/114.02, 114.16, 35.01–35.6; 701/111
See application file for complete search history.

(56) References Cited

U.S. PATENT DOCUMENTS

| | | | | | |
|---|---|---|---|---|---|
| 3,318,136 | A | * | 5/1967 | Payne | G01N 33/2817 73/35.02 |
| 4,010,358 | A | * | 3/1977 | Morris | G01N 33/2817 702/30 |
| 4,331,024 | A | * | 5/1982 | Childs | G01N 33/2817 73/35.02 |
| 5,633,798 | A | * | 5/1997 | Kopp | G01N 33/2829 73/114.38 |
| 2015/0120211 | A1 | * | 4/2015 | Michaelis | G01N 33/22 702/22 |

(Continued)

*Primary Examiner* — Scott A Reinbold
(74) *Attorney, Agent, or Firm* — Vorys, Sater, Seymour, and Pease LLP

(57) ABSTRACT

A method of assigning an octane number to a sample fuel based on the knock intensities obtained from a plurality of reference fuels each having a different assigned octane number while operating an engine at an established compression ratio. The knock intensities obtained from the plurality of reference fuels are plotted relative to the assigned octane numbers of the fuels. A line is fit to the plotted knock intensities. The octane number for a sample fuel is assigned based on the knock intensity obtained for the sample fuel, the knock intensity obtained from a prototype fuel having an assigned octane number, and the fitted line. In embodiments, an R squared value is obtained for the fitted line and compared with a minimum acceptable R squared value and the fitted line is validated if the R squared value is at least the minimum acceptable R squared value.

12 Claims, 1 Drawing Sheet

(56) References Cited

U.S. PATENT DOCUMENTS

2016/0326976 A1\* 11/2016 Huber .................. F02D 35/027
2018/0216428 A1\* 8/2018 Sinn ..................... E21B 21/062

\* cited by examiner

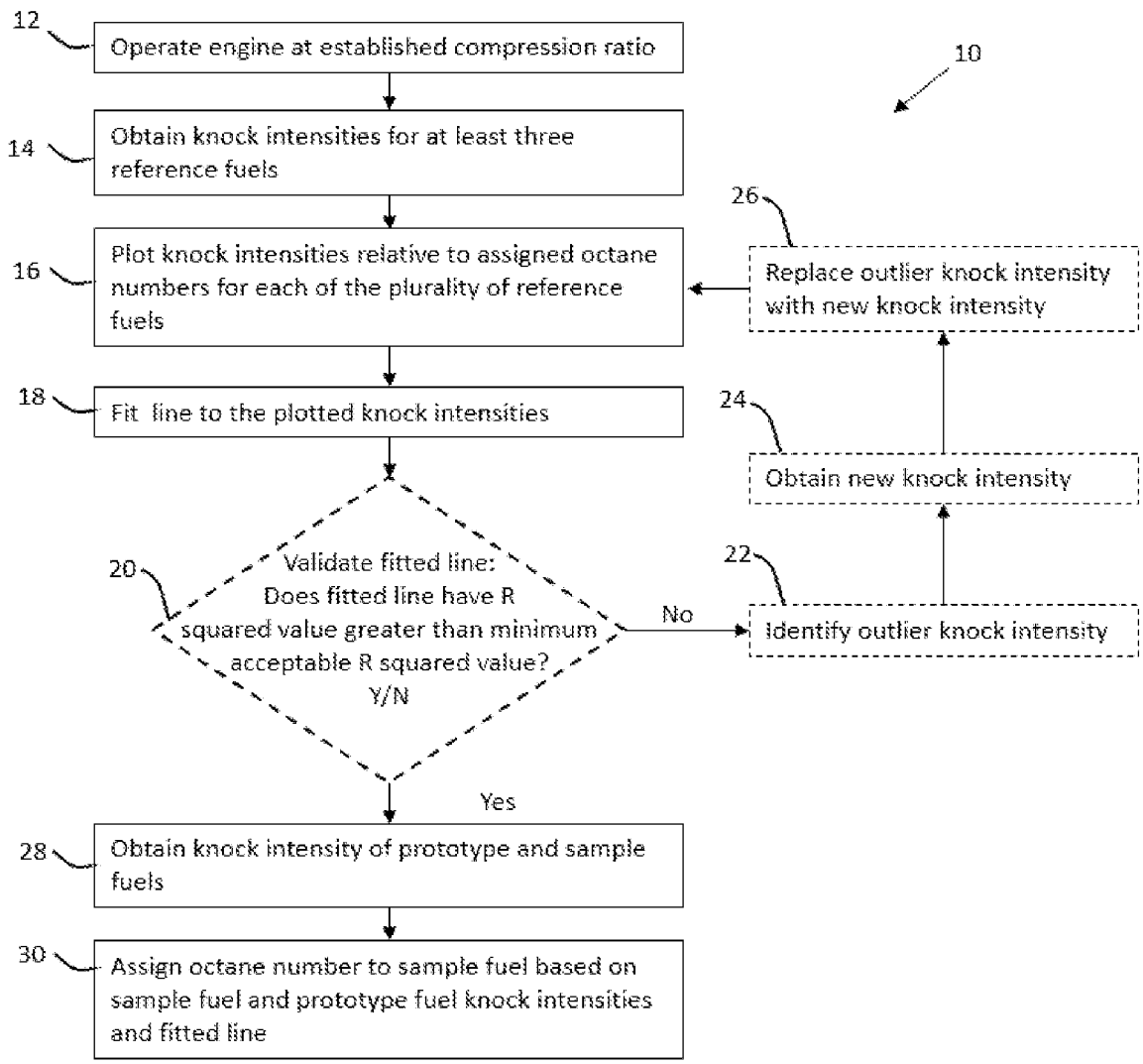

METHOD OF ASSIGNING AN OCTANE NUMBER TO A FUEL

CROSS REFERENCE TO RELATED APPLICATION

This application relates and claims priority to U.S. Provisional Patent Application No. 62/970,221 filed on Feb. 5, 2020, which is incorporated herein specifically by reference.

BACKGROUND

The present disclosure relates to methods of assigning an octane number to a fuel.

The octane number for a fuel is a standard measure of performance for fuels that relates to the compression at which the fuel will ignite. The higher the octane number, the more resistant the fuel is to igniting. Most internal combustion engines are built to run on fuels having a standard octane rating. If the octane rating of a fuel is too low, the fuel may ignite too early in the initiation process causing a knock, which can damage the engine.

Petrochemical fuels are mixtures of hydrocarbons. The relative percentages of the different hydrocarbons in the fuels will determine the octane number of the fuel. To prepare a blend of petrochemical fuels having an octane rating suitable for safe use in internal combustion engines, fuel manufacturers blend stocks of distilled fuels into a sample fuel and then compare the sample (blended) fuel with prototype fuels to assign an octane number to the blended fuel. Typically, the octane number for blended fuel is assigned in a test engine using a standardized procedure such as ASTM D2885.

In particular, ASTM D2885 may be used to assign an octane number to a blended fuel by difference comparing it to a comparison reference fuel, which is also known as a prototype reference fuel, having an assigned octane number. For this procedure, a test engine is operated on a pair of primary reference fuels having a difference of 1.0+/−0.2 octane number at a compression ratio that is optimized for the assigned octane number of one of the primary reference fuels. These measurements are used to calculate the knock intensity units per octane number (spread) of the test engine for the octane range defined by the two primary reference fuels. After calculating the knock intensity units per octane number of the test engine, the knock intensities for the blended fuel and a prototype fuel having an assigned octane number are obtained in the test engine. However, since the octane measurement scale is not linear, this procedure requires that the octane number of the blended fuel must fall within +/−1 octane number of the prototype fuel for certification of the blended fuel's octane number. If the octane number for the blended fuel is outside the +/−1 octane number range, the test is not a valid result and cannot be used to represent the blended product. Since the octane number of the blended fuel must fall within +/−1 octane number of the prototype fuels, blending facilities must manage numerous prototype fuels with different octane numbers to cover the full range of gasoline grades.

SUMMARY

The present disclosure relates to methods of assigning an octane number to a sample fuel.

A method of the present disclosure can include assigning an octane number to a sample fuel based on the knock intensities obtained from at least three reference fuels each having a different assigned octane number while operating an engine at an established compression ratio. The knock intensities obtained from the reference fuels are plotted relative to the assigned octane numbers of the fuels. A line is fit to the plotted knock intensities. The knock intensities for a prototype fuel having an assigned octane value and a sample fuel are obtained while operating the engine at the same compression ratio as the reference fuels. The octane number for the sample fuel is assigned based on the knock intensities obtained for the sample fuel, the prototype fuel, and the fitted line. In embodiments, an R squared value is obtained for the fitted line and compared with a minimum acceptable R squared value and the fitted line is validated if the R squared value is at least the minimum acceptable R squared value.

Another method of the present disclosure can include: operating an engine at an established compression ratio; obtaining a first knock intensity while operating the engine on a first reference fuel having a first assigned octane number, obtaining a second knock intensity while operating the engine on a second reference fuel having a second assigned octane number, obtaining a third knock intensity while operating the engine on a third reference fuel having a third assigned octane number, and obtaining a fourth knock intensity while operating the engine on a fourth reference fuel having a fourth assigned octane number. The first, second, third, and fourth knock intensities are plotted relative to their respective first, second, third, and fourth assigned octane numbers and a line is fit to the plotted first, second, third, and fourth knock intensities. An R squared value is obtained for the fitted line and the R squared value is compared with a minimum acceptable R squared value, and the fitted line is validated if the R squared value is at least the minimum acceptable R squared. The engine is operated on a prototype fuel and a sample fuel and prototype and sample knock intensities are obtained. If the fitted line is validated, the octane number of the sample fuel is assigned based on the prototype fuel knock intensity, the sample knock intensity, and the fitted line.

BRIEF DESCRIPTION OF THE DRAWING

The following FIGURE is included to illustrate certain aspects of the embodiments and should not be viewed as an exclusive embodiment. The subject matter disclosed is capable of considerable modifications, alterations, combinations, and equivalents in form and function, as will occur to those skilled in the art and having the benefit of this disclosure.

The FIG. 1 is a flow chart illustrating steps for assigning an octane number to a sample fuel in accordance with embodiments of the present disclosure.

DETAILED DESCRIPTION

The present disclosure relates to assigning an octane number to a sample fuel, which can include blends of fuels, using at least three reference fuels run through a test engine operating at a constant established compression ratio. The present methods generate a linear knock intensity/octane number curve over an octane number range that allows the difference between the sample fuel and the prototype fuels required for certification to increase up to +/−4 octane number (as opposed to +/−1 octane number for ASTM D2885). This increase in the sample fuel to prototype fuel difference can decrease the number of prototype fuels that a blending facility is required to manage and increase the proper certification of blends. Accordingly, this new method increases the operating efficiency of blending facilities as they assign octane numbers to sample fuels.

Generally speaking, the methods obtain a linear knock intensity/octane number curve using at least three different reference fuels. The line fit to this curve may be used to assign an octane number to the sample fuel.

With reference to the FIGURE, the method 10 includes operating a test engine at an established compression ratio (block 12). The established compression ratio of the test engine is kept constant while the engine is operated on each of the reference fuels and the sample fuel. The established compression ratio is selected based on the assigned octane numbers of the reference fuels. By way of example, where three reference fuels are used, the established compression ratio may be based on the optimal compression ratio for the assigned octane number of one of the reference fuels, generally the compression ratio chosen is that of the reference fuel having the middle octane number (that is, not the highest or the lowest octane number of the three reference fuels). Where four reference fuels are used, the established compression ratio is based on the octane number of the reference fuel having the next to lowest or the next to highest assigned octane number. In other cases, the established compression ratio is not based on the optimal compression of one of the reference fuels, but is instead based on an average or calculated middle range octane number calculated from the octane numbers of two or more of the references fuels.

At block 14, the knock intensities for at least three reference fuels is obtained. The operating parameters for obtaining knock intensities in an engine are well known to those of ordinary skill in the art and are not recounted here in great detail. However, generally speaking, obtaining the knock intensity from the test engine includes operating the engine on a reference fuel, a prototype fuel, or a sample fuel for a duration of time while collecting data on the knock intensity and calculating a knock intensity for the fuel. Knock intensity data in the engine may be collected with a detonation meter and knock meter. Embodiments of the present disclosure utilize detonation meters and knock meters capable of providing a linear response over a wide range of knock intensities. In an embodiment, the knock intensity range is between 0 KI to 250 KI. In another embodiment, the knock intensity range is between 0 KI and 200 KI.

At least three reference fuels are used so that the linearity of the knock intensity/octane number curve can be verified. Each reference fuel has a different assigned octane number. As the octane numbers for the reference fuels increases, the difference in octane number values from one reference fuel to the next will decrease. Thus, the two reference fuels having the lowest octane numbers will have a greater difference in octane between them than the two reference fuels having the highest octane numbers. In some cases, the reference fuels will have assigned octane numbers that differ from one another by a value of at least 0.5 octane number, or by a value not greater than 2.5 octane number. In yet another embodiment, the reference fuels will have assigned octane numbers that differ from one another by a value in a range from 0.5 octane number to 2.5 octane number. The assigned octane number of the reference fuel with the lowest octane number should differ from the assigned octane number of the reference fuel with the highest octane number by a value that is in a range from 2.5 octane number and 8 octane number.

Reference fuels are typically blends of fuels having a known blend of hydrocarbons and assigned octane numbers such as primary reference fuels. Exemplary reference fuels are toluene standard fuels that are mixed based on calculations to obtain reference fuels with the desired assigned octane numbers.

The order that the reference fuels are run through the engine may affect the operating temperature of the engine and the data collected. Without being limited by theory, if the reference fuels are run in an order from lowest octane number to highest octane number, or conversely, from highest octane number to lowest octane number, the order may introduce a bias into the data collected. To account for this potential bias, embodiments of the present disclosure randomize the order in which the reference fuels are run through the engine such that a reference fuels is not run through the engine immediately before or immediately after a reference fuel having the next highest or next lowest octane number. For example, if there are three reference fuels, the reference fuel with the middle assigned octane number will be run through the engine either first or last with the reference fuels having the highest and lowest octane numbers being run consecutive to one another either before or after the reference fuel with the middle octane number. For example, the engine is operated on a first reference fuel, a second reference fuel, a third reference fuel, and a fourth reference fuel, and the second reference fuel has the lowest assigned octane number, the fourth reference fuel has the highest assigned octane number, and the first reference fuel has an assigned octane number that is greater than the assigned octane number of the third reference fuel. In another example, the engine is operated on a first reference fuel, a second reference fuel, a third reference fuel, and a fourth reference fuel, wherein the second reference fuel has the highest assigned octane number, the fourth reference fuel has the lowest assigned octane number, and the first reference fuel has an assigned octane number that is less than the assigned octane number of the third reference fuel.

At blocks 16 and 18, the knock intensities for the reference fuels are plotted relative to their respective assigned octane numbers and a line is fit to the plotted knock intensities. The knock intensities may be plotted and lines fit using standard data analysis software. In embodiments, the line may be fit using a linear method, a polynomial method, or both a linear method and a polynomial method. Fitting the line may also include obtaining a linear formula, a polynomial formula, or both a linear formula and a polynomial formula for the fitted line.

At block 20, the line may be verified. In an embodiment, an R squared value is obtained for the line and the R squared value is compared to a minimum acceptable R squared value. If the R squared value of the line is at least the minimum acceptable R squared value then the line is validated. If the R squared value of the line is less than the minimum acceptable R squared value then the line is not validated. In an embodiment, the minimum acceptable R squared value is at least 95. In another embodiment, the minimum acceptable R squared value is at least 98.9. In yet another embodiment, the minimum acceptable R squared value is 99.

In embodiments requiring validation, if the line is not validated, a new line will need to be generated before an octane number can be assigned to a sample fuel. In an embodiment, a new line may be generated by starting over at block 14. In another embodiment, the knock intensity that resulted in the line not being validated is identified (block 22) and a new knock intensity is obtained from a reference fuel having the same assigned octane number as the reference fuel that resulted in the outlier knock intensity (block 24). This may require the operator to obtain a different or newly mixed version of the reference fuel. The outlier knock intensity is then replaced with the new knock intensity (block 26) and the knock intensities are plotted (block 16), a line is fit (block 18), and the validation process is repeated (block 20).

Once the line is fit and validated (when required), the engine is operated on a prototype fuel having an assigned octane number and the sample fuel and the knock intensities for the fuels are obtained (block 28). The engine is operated on the prototype fuel and the sample fuel at the same established compression ratio as was used with the reference fuels. Using the knock intensity from the prototype fuel, the sample fuel and the fitted line, an octane number is assigned to the sample fuel. In an embodiment, the knock intensities for the prototype fuel and the sample fuel may be inserted into the linear formula, the polynomial formula, or both the linear and polynomial formulas to calculate and assign the octane number to the sample fuel. Alternatively, the octane number for the sample fuel could be assigned based on octane number coordinate along the line that corresponds to the knock intensity of the sample fuel.

The methods described herein may be used to assign a research octane number (RON), a motor octane number (MON), or both a RON and a MON to a sample fuel. RON and MON may be assigned by standard methods such as ASTM D2699 for RON and ASTM D2700 for MON.

Embodiments of the method may be performed on a computer system. An exemplary computer system suitable for use with embodiments of the invention includes a processor, memory, a display, an input device such as a keyboard or touchscreen, and optional connectivity to other computer systems such as wireless or wired connections over the internet as well as connectivity to sources of knock intensity data such as with the detonation meters and knock meters. Additionally, embodiments of the method may include a computer program having coding that performs the analytical steps of the method.

Example Embodiment

A non-limiting example embody of the present disclosure is a method comprising: operating an engine at an established compression ratio; obtaining a first knock intensity while operating the engine on a first reference fuel having a first assigned octane number, obtaining a second knock intensity while operating the engine on a second reference fuel having a second assigned octane number, obtaining a third knock intensity while operating the engine on a third reference fuel having a third assigned octane number, and obtaining a fourth knock intensity while operating the engine on a fourth reference fuel having a fourth assigned octane number. The method further comprises plotting the first, second, third, and fourth knock intensities relative to their respective first, second, third, and fourth assigned octane numbers and fitting a line to the plotted first, second, third, and fourth knock intensities. The line is fit using both linear and polynomial methods and linear and polynomial formulas for the fitted lines are obtained. The R squared values of the lines are compared with a minimum acceptable R squared value and the line is validated if the R squared value is at least the minimum acceptable R squared value. The minimum R squared value in this example is 99. Knock intensities for a prototype fuel and a sample fuel is obtained while operating the engine on the prototype fuel or the sample fuel. The knock intensities for the prototype fuel and the sample fuel are used to assign an octane number to the sample fuel. When the linear fit equation is used, the fitted line is used to determine the spread of the engine for the octane range of the fuels within the calibration set. The difference between the knock intensity reading of the prototype fuels and the sample fuels (prototype KI—sample KI) are divided by the spread determined by the fitted line to determine the delta between the two fuels. The delta between the sample fuel and the prototype fuel is then added onto the assigned octane value of the prototype fuel to produce an octane number.

Unless otherwise indicated, all numbers expressing quantities, properties, operating conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present disclosure. At the very least, and not as an attempt to limit the application of the doctrine of equivalents to the scope of the claim, each numerical parameter should at least be construed in light of the number of reported significant digits and by applying ordinary rounding techniques.

One or more illustrative embodiments incorporating the invention embodiments disclosed herein are presented herein. Not all features of a physical implementation are described or shown in this application for the sake of clarity. It is understood that in the development of a physical embodiment incorporating the embodiments of the present invention, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

While embodiments are described herein in terms of "comprising" various components or steps, the embodiments can also "consist essentially of" or "consist of" the various components and steps.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of the methods herein described, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein. While embodiments are described in terms of "comprising," "containing," or "including" various components or steps, the embodiments can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from a to b," or, equivalently, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

The invention claimed is:

1. A method of assigning an octane number of a sample fuel, the method comprising:
   operating an engine at a constant established compression ratio;
   obtaining a plurality of knock intensities while operating the engine on at least three reference fuels, wherein each reference fuel has an assigned octane number that differ from each other by a value of no less than 0.5 octane number and no greater than 2.5 octane number, thereby having at least first reference fuel having a highest octane number, a second fuel having a middle octane number, and a third reference fuel having a lowest octane number, and
   wherein the constant established compression ratio is based on the second reference fuel and the knock intensities are in the range of 0 KI to 250 KI;
   plotting the plurality of knock intensities relative to their respective assigned octane numbers;
   fitting a line to the plotted plurality of knock intensities with a linear method to determine a spread of the engine based on calculating knock intensity units per octane number of the engine for the at least three reference fuels;
   obtaining a prototype fuel knock intensity while operating the engine on a prototype fuel having an assigned octane number;
   obtaining a sample fuel knock intensity while operating the engine on the sample fuel having an unassigned octane number, and wherein the prototype fuel and the sample fuel differ from each another up to +/−4 octane number; and
   assigning an octane number of the sample fuel based on the prototype fuel knock intensity, the sample fuel knock intensity, and the fitted line,
   wherein the assigning is based on dividing a difference between the prototype fuel knock intensity and the sample knock intensity by the spread to determine a delta between the sample fuel and the prototype fuel, and adding the delta to the obtained octane number of the prototype fuel.

2. The method of claim 1, wherein fitting the line further comprises obtaining an R squared value for the fitted line, comparing the R squared value with a minimum acceptable R squared value, and validating the fitted line if the R squared value is at least the minimum acceptable R squared value.

3. The method of claim 2, wherein the minimum acceptable R squared value is at least 95.

4. The method of claim 2, wherein the minimum acceptable R squared value is at least 98.9.

5. The method of claim 2, wherein if the R squared value is less than the minimum acceptable R squared value,
   identifying as an outlier knock intensity the knock intensity from the plurality of knock intensities that resulted in the R squared value being less than the minimum acceptable R squared value,
   obtaining a new knock intensity for a reference fuel having an assigned octane number that is the same as the assigned octane number of the reference fuel that resulted in the outlier knock intensity;
   replacing with outlier knock intensity with the new knock intensity;
   plotting the new knock intensity with the remaining of the plurality of knock intensities; fitting an updated line to the plotted the knock intensities with the linear method; and
   assigning the octane number of the sample fuel based on the prototype fuel knock intensity, the sample knock intensity, and the fitted line.

6. The method of claim 1, wherein the established compression ratio is based on the assigned octane number of one of the at least three reference fuels.

7. The method of claim 1, wherein the at least three reference fuels are toluene standard fuels.

8. The method of claim 1, wherein the assigned octane number of the third reference fuel having the lowest octane number differs from the assigned octane number of the first reference fuel having the highest octane number by a value that is in a range from 2.5 octane number and 8 octane number.

9. The method of claim 1, wherein fitting the line further includes fitting the line with a polynomial method.

10. The method of claim 1, wherein fitting the line includes obtaining a linear formula, a polynomial formula, or both a linear formula and a polynomial formula for the fitted line.

11. A method of obtaining an octane number of a first fuel, the method comprising:
   operating an engine at a constant established compression ratio;
   obtaining a first knock intensity while operating the engine on a first reference fuel having a first assigned octane number,
   obtaining a second knock intensity while operating the engine on a second reference fuel having a second assigned octane number,
   obtaining a third knock intensity while operating the engine on a third reference fuel having a third assigned octane number, and
   obtaining a fourth knock intensity while operating the engine on a fourth reference fuel having a fourth assigned octane number,
      wherein each of the the first assigned octane number, the second assigned octane number, the third assigned octane number, and the fourth assigned octane number differ from each other by a value of no less than 0.5 octane number and no greater than 2.5 octane number,
      wherein the second assigned octane number has a lowest assigned octane number, the fourth assigned octane number has a highest assigned octane number, and the first assigned octane number that is greater than the assigned octane number of the third reference fuel, and
   wherein the constant established compression ratio is based on the first reference fuel or the third reference fuel and the knock intensities are in the range of 0 KI to 250 KI;
   running the first, second, third, and fourth reference fuels through the engine in an order in which fuels with the next highest or next lowest octane number are not run consecutive with one another;

plotting the first, second, third, and fourth knock intensities relative to their respective first, second, third, and fourth assigned octane numbers;

fitting a line to the plotted first, second, third, and fourth knock intensities with a linear method to determine a spread of the engine based on calculating knock intensity units per octane number of the engine for the at least three reference fuels;

obtaining an R squared value for the fitted line, comparing the R squared value with a minimum acceptable R squared value, and validating the fitted line if the R squared value is at least the minimum acceptable R squared value;

obtaining a prototype fuel knock intensity while operating the engine on a prototype fuel having an assigned octane number;

obtaining a sample fuel knock intensity while operating the engine on the sample fuel having an unassigned octane number, and wherein the prototype fuel and the sample fuel differ from one another by up to +/−4 octane number; and if the fitted line is validated, assigning an octane number of the sample fuel based on the prototype fuel knock intensity, the sample fuel knock intensity, and the fitted line, wherein the assigning is based on dividing a difference between the prototype fuel knock intensity and the sample knock intensity by the spread to determine a delta between the sample fuel and the prototype fuel, and adding the delta to the obtained octane number of the prototype fuel.

12. The method of claim 11, wherein the minimum acceptable R squared value is at least 95.

* * * * *